US00PP21021P2

(12) United States Plant Patent
Blom

(10) Patent No.: US PP21,021 P2
(45) Date of Patent: May 25, 2010

(54) CAMPANULA PLANT NAMED 'VIKING'
(50) Latin Name: *Campanula hybrida*
Varietal Denomination: Viking

(76) Inventor: Arie Blom, Waterbieslaan 110, 3452 AR Vleuten (NL)

( * ) Notice: Subject to any disclaimer, the term of this patent is extended or adjusted under 35 U.S.C. 154(b) by 0 days.

(21) Appl. No.: 12/319,414

(22) Filed: Jan. 7, 2009

(51) Int. Cl.
*A01H 5/00* (2006.01)

(52) U.S. Cl. ..... Plt./414
(58) Field of Classification Search ..... Plt./414
See application file for complete search history.

*Primary Examiner*—June Hwu
(74) *Attorney, Agent, or Firm*—C. A. Whealy

(57) ABSTRACT

A new and distinct cultivar of *Campanula* plant named 'Viking', characterized by its upright plant habit; freely basal branching habit; freely flowering habit; and violet-colored campanulate-shaped flowers.

2 Drawing Sheets

Botanical designation: *Campanula hybrida.*
Cultivar denomination: 'VIKING'.

BACKGROUND OF THE INVENTION

The present invention relates to a new and distinct cultivar of *Campanula* plant, botanically known as *Campanula hybrida* and hereinafter referred to by the name 'Viking'.

The new *Campanula* plant originated from a cross-pollination in IJsselstein, The Netherlands in May, 2004, of a proprietary selection of *Campanula hybrida* identified as code number Ca 402-01, not patented, as the female, or seed, parent with a proprietary selection of *Campanula hybrida* identified as code number Ca 406-01, not patented, as the male, or pollen, parent. The new *Campanula* was discovered and selected by the Inventor as a single flowering plant from within the progeny of the stated cross-pollination grown in a controlled greenhouse environment in Zuidwolde, The Netherlands in June, 2007.

Asexual reproduction of the new *Campanula* plant by tissue culture in The Netherlands, since October, 2007, has shown that the unique features of this new *Campanula* plant are stable and reproduced true to type in successive generations.

SUMMARY OF THE INVENTION

Plants of the new *Campanula* have not been observed under all possible environmental conditions. The phenotype may vary somewhat with variations in environment such as temperature and light intensity without, however, any variance in genotype.

The following traits have been repeatedly observed and are determined to be the unique characteristics of 'Viking'. These characteristics in combination distinguish 'Viking' as a new and distinct cultivar:

1. Upright plant habit.
2. Freely basal branching habit.
3. Freely flowering habit.
4. Violet-colored campanulate-shaped flowers.

Plants of the new *Campanula* differ from plants of the female parent selection in the following characteristics:

1. Plants of the new *Campanula* have longer flowering stems than plants of the female parent selection.

2. Plants of the new *Campanula* have larger leaves than plants of the female parent selection.
3. Plants of the new *Campanula* flower for a longer period of time than plants of the female parent selection.

Plants of the new *Campanula* differ from plants of the male parent selection in the following characteristics:

1. Plants of the new *Campanula* have lighter green-colored leaves than plants of the male parent selection.
2. Plants of the new *Campanula* are more freely flowering than plants of the male parent selection.
3 . Plants of the new *Campanula* have larger flowers than plants of the male parent selection.

Plants of the new *Campanula* can be compared to plants of *Campanula* 'Sarastro', not patented. In side-by-side comparisons, plants of the new *Campanula* differed from plants of 'Sarastro' in the following characteristics:

1. Plants of the new *Campanula* were more compact than plants of 'Sarastro'.
2. Plants of the new *Campanula* were more freely flowering than plants of 'Sarastro'.
3. Plants of the new *Campanula* had violet-colored flowers whereas plants of 'Sarastro' had dark purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Campanula.*

The photograph on the first sheet is a side perspective view of a typical flowering plant of 'Viking' grown in a container.

The photograph at the top of the second sheet is a close-up view of typical flowers of 'Viking'.

The photograph at the bottom of the second sheet is a close-up view of the upper surface of a typical leaf of 'Viking'.

DETAILED BOTANICAL DESCRIPTION

Plants used for the aforementioned photographs and following description were grown under conditions which closely approximate commercial production conditions during the summer in an outdoor nursery in Zuidwolde, The Netherlands. During the production of the plants, day temperatures ranged from 14° C. to 32° C. and night temperatures ranged from 6° C. to 18° C. Plants had been growing for six months when the photographs and description were taken. In the following description, color references are made to The Royal Horticultural Society Colour Chart, 2001 Edition, except where general terms of ordinary dictionary significance are used.

Botanical classification: *Campanula hybrida* 'Viking'.

Parentage:

*Female parent.*—Proprietary selection of *Campanula hybrida* identified as code number Ca 402-01, not patented.

*Male parent.*—Proprietary selection of *Campanula hybrida* identified as code number Ca 406-01, not patented.

Propagation:

*Type.*—By tissue culture.

*Time to initiate roots.*—About ten days at 25° C.

*Time to produce a rooted young plant.*—About 35 days at 21° C.

*Root description.*—Fine, fibrous; pale cream in color.

*Rooting habit.*—Freely branching; dense.

Plant description:

*Form.*—Herbaceous perennial; upright plant habit; freely basal branching habit with about nine basal branches developing per plant; moderately vigorous growth habit; campanulate flowers arranged in compound racemes.

*Plant height.*—About 47.4 cm.

*Plant width.*—About 46.8 cm.

*Basal branch description.*—Length (to top of foliar plane): About 25.7 cm. Length (to top of inflorescences): About 47.4 cm. Diameter: About 4 mm. Internode length: About 3.7 cm. Strength: Strong. Texture: Pubescent. Color: Close to 145A tinged with close to 199A.

Foliage description:

*Arrangement.*—Alternate, simple.

*Length.*—About 9.8 cm.

*Width.*—About 5.5 cm.

*Shape.*—Ovate.

*Apex.*—Acute.

*Base.*—Cordate to obtuse.

*Margin.*—Serrate.

*Texture, upper and lower surfaces.*—Pubescent.

*Venation pattern.*—Pinnate.

*Color.*—Developing leaves, upper surface: Close to 143A. Developing leaves, lower surface: Close to 143C. Fully expanded foliage, upper surface: Close to 137A; venation, 144A. Fully expanded foliage, lower surface: Close to 137C; venation, close to 144D.

*Petiole length.*—About 8.7 cm.

*Petiole diameter.*—About 4 mm.

*Petiole texture, upper and lower surfaces.*—Pubescent.

*Petiole color, upper and lower surfaces.*—Close to 146C.

Flower description:

*Flower arrangement and shape.*—Single campanulate star-shaped flowers arranged in compound racemes; flowers face mostly outwardly to drooping; freely flowering habit, about 36 flowers develop per inflorescence.

*Natural flowering season.*—Continuous flowering from late July to late September in The Netherlands.

*Flower longevity on the plant.*—About ten days; flowers persistent.

*Fragrance.*—None detected.

*Inflorescence height.*—About 18.7 cm.

*Inflorescence diameter.*—About 12.5 cm.

*Flower buds.*—Length: About 3.4 cm. Diameter: About 7 mm. Shape: Narrowly oblong to obovate. Color: Close to N77A.

*Flowers.*—Diameter: About 4.4 cm. Depth (height): About 5.2 cm.

*Petals.*—Arrangement: Five to six in a single whorl; fused. Length: About 5 cm. Width: About 1.1 cm. Shape: Narrowly oblong; lobe, ovate. Apex: Acute. Margin: Entire. Texture, upper and lower surfaces: Pubescent. Color: When opening, upper surface: Close to 86D; towards the apex, close to N87C; venation, close to 86D. When opening, lower surface: Between N87C and N88C; venation, close to N79C. Fully opened, upper surface: Close to 86D; towards the apex, close to 86B to 86C; venation, close to 86D; color becoming close to 86B to 86C with development. Fully opened, lower surface: Close to 86C; venation, close to N79C.

*Sepals.*—Arrangement: Five in a single whorl; fused. Length: About 2.3 cm. Width: About 6 mm. Shape: Lanceolate. Apex: Acute. Margin: Entire. Texture, upper and lower surfaces: Pubescent. Color, upper and lower surfaces: Close to 144B; towards the apex, close to 146B to 146C.

*Peduncles.*—Length: About 14.4 cm. Diameter: About 3.5 mm. Aspect: Upright. Strength: Strong. Texture: Pubescent. Color: Close to 145A tinted with close to 199A.

*Pedicels.*—Length: About 3 mm. Diameter: About 1 mm. Aspect: Close to 40° from vertical. Strength: Strong. Texture: Pubescent. Color: Close to 145A tinted with close to 199A.

*Reproductive organs.*—Stamens: Quantity per flower: Five. Anther shape: Narrowly lanceolate. Anther length: About 8 mm. Anther color: Close to 22C. Filament length: About 3 mm. Filament color: Close to N155A. Pollen amount: Scarce to moderate. Pollen color: Close to 8D. Pistils: Quantity per flower: One. Pistil length: About 3.2 cm. Stigma shape: Narrowly lanceolate. Stigma color: Close to 155C. Style length: About 3 cm. Style color: Towards the apex, close to N87D; towards the base, close to 155C. Ovary color: Close to 144B to 144C.

*Seed/fruit.*—Seed and fruit production have not been observed.

Disease/pest resistance: Plants of the new *Campanula* have not been noted to be resistant to pathogens and pests common to *Campanula*.

Garden performance: Plants of the new *Campanula* have exhibited good tolerance to rain and wind and have been observed to tolerate temperatures ranging from about −20° C. to about 45° C.

It is claimed:

1. A new and distinct *Campanula* plant named 'Viking' as illustrated and described.

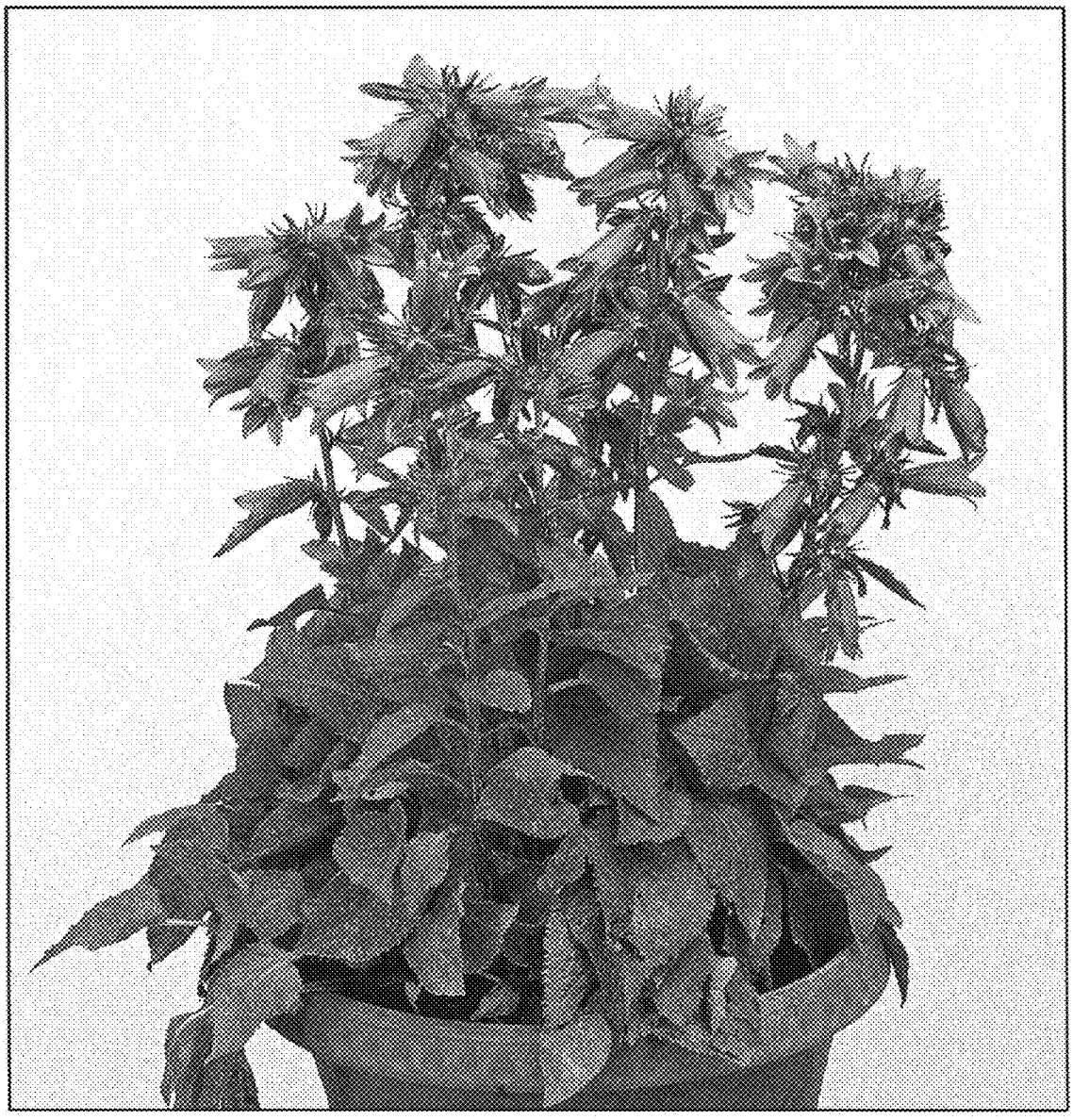

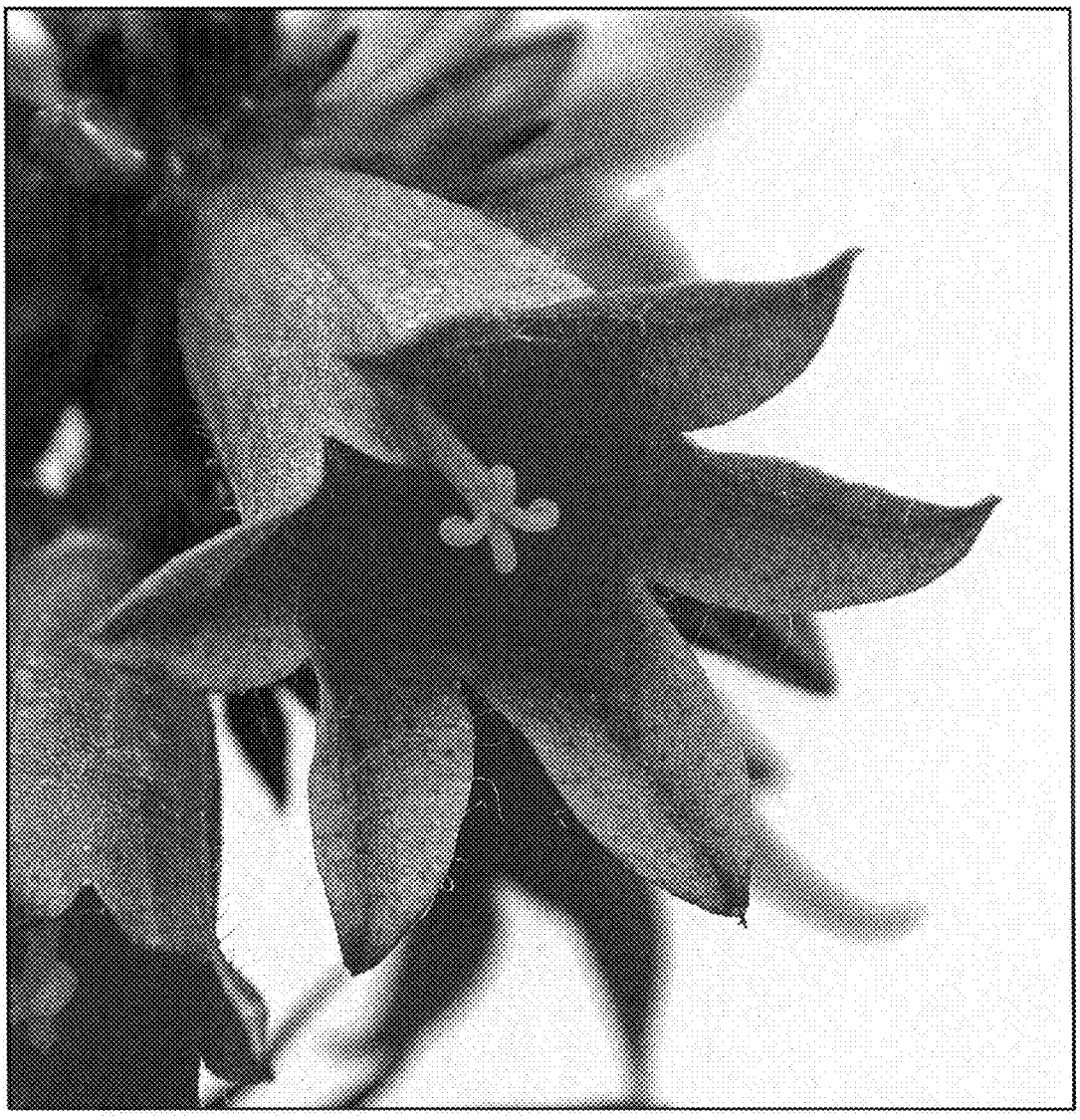
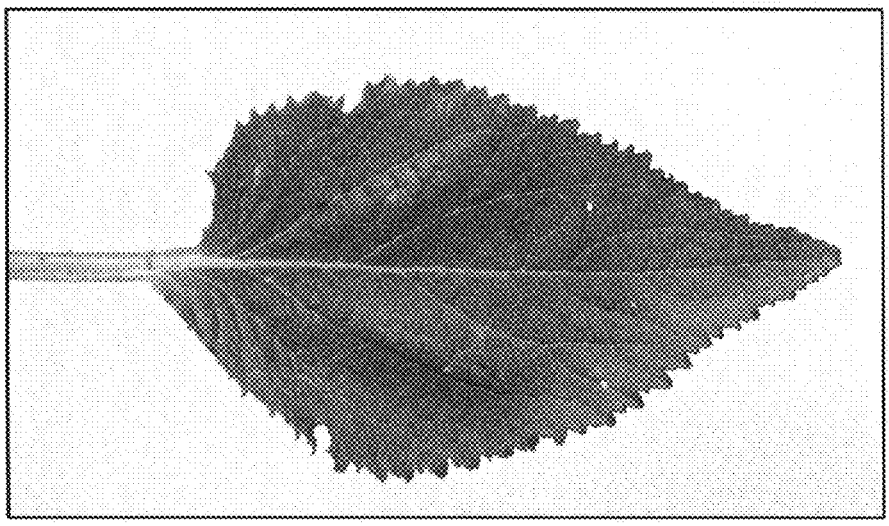

* * * * *